(12) United States Patent
Pola

(10) Patent No.: US 7,211,571 B2
(45) Date of Patent: May 1, 2007

(54) COMPOSITION FOR THE PREVENTION AND/OR TREATMENT OF LIPID METABOLISM DISORDERS AND ALLERGIC FORMS

(75) Inventor: Pietro Pola, Rome (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 33 days.

(21) Appl. No.: 10/181,262

(22) PCT Filed: Jul. 24, 2001

(86) PCT No.: PCT/IT01/00394

§ 371 (c)(1),
(2), (4) Date: Jul. 16, 2002

(87) PCT Pub. No.: WO02/40012

PCT Pub. Date: May 23, 2002

(65) Prior Publication Data

US 2003/0017999 A1     Jan. 23, 2003

(30) Foreign Application Priority Data

Nov. 17, 2000  (IT)  .......................... RM2000A0602

(51) Int. Cl.
*A61K 31/715*  (2006.01)
*A61K 31/716*  (2006.01)
*A61K 31/205*  (2006.01)
*C07H 1/00*  (2006.01)

(52) U.S. Cl. ........................................ 514/54; 514/556

(58) Field of Classification Search .................. 514/54, 514/556; 536/123.1, 123.12
See application file for complete search history.

(56) References Cited

U.S. PATENT DOCUMENTS

| 4,975,421 A | * | 12/1990 | Williams et al. ............... 514/54 |
| 5,977,073 A | * | 11/1999 | Khaled ......................... 514/19 |
| 6,037,373 A | * | 3/2000 | De Simone .................. 514/556 |
| 6,080,788 A | * | 6/2000 | Sole et al. ................... 514/561 |
| 6,217,898 B1 | | 4/2001 | Cavazza |

FOREIGN PATENT DOCUMENTS

| EP | 0 951 909 A | | 10/1999 |
| WO | WO 97/02356 | * | 1/1997 |
| WO | WO 97/05864 | * | 2/1997 |
| WO | 01/43758 A | | 6/2001 |

OTHER PUBLICATIONS

Estrada et al (Microbiol. Immunol. 41(12):991-998 (1997)).*
Gonda et al (Chem. Pharm. Bull. 38(10:2771-2774 (1990)).*
Gonda et al (Chem. Pharm. Bull. 39(2):441-444 (1991)).*

* cited by examiner

*Primary Examiner*—Ruth A. Davis
(74) *Attorney, Agent, or Firm*—Nixon & Vanderhye P.C.

(57) ABSTRACT

A composition is disclosed which can be used as a health food/dietary supplement or as a drug for the prevention and/or treatment of lipid metabolism disorders and allergic forms and for activating organic defences against infections and tumor processes, containing as its characterizing components isovaleryl L-carnitine and a polysaccharide selected from glucans and galactans.

21 Claims, No Drawings

COMPOSITION FOR THE PREVENTION AND/OR TREATMENT OF LIPID METABOLISM DISORDERS AND ALLERGIC FORMS

The present invention relates to a composition suitable for the prevention and/or treatment of lipid metabolism disorders and allergic forms and for activating immune defences.

Accordingly, the composition may take the form and exert the activity of a health food or of an actual medicine, depending upon the supporting or preventive action or the more strictly therapeutic action which the composition is intended to exert according to the particular individuals in whom it is to be used.

More particularly, the composition according to the invention comprises the following as its characterising active ingredients:

(a) isovaleryl L-carnitine or one of its pharmacologically acceptable salts, and
(b) a polysaccharide selected from the group consisting of phosphorylated, glycosylated or aminated glucans and galactans, or mixtures thereof.

It has been found that the above-mentioned composition is extremely effective in exerting a potent preventive/curative action on the disorders previously indicated and in activating immune and organic defences against bacterial or viral infections and tumour processes as a result of the unexpected synergistic effect exerted by the interaction between its components.

Isovaleryl L-carnitine belongs to the organic pool of carnitines, but distinguishes itself from the other alkanoyl L-carnitines in its ability to inhibit, in a number of organs such as the liver, the lysosomal proteases induced by a deficiency in amino acids and in its regulation of the calpain system and its activation of calpases which play an important role mediated by calcium in cell activity and survival. Like the other alkanoyl L-carnitines, it exerts an important metabolic action in the production of energy via the β-oxidation of fatty acids as well as an important antilipoperoxidative and cardiovascular protective activity.

β-glucans have long been known for their antiatherosclerotic and cardioprotective activity. β-glucan is a soluble fibre present in oat bran and used for some years now as a health food for controlling hypercholesterolaemia. Among the more recent findings regarding the mechanism of these activities of β-glucan, there has been one that indicates a particular ability of β-glucan to bind to specific receptors located on the surface of macrophages and to stimulate their phagocyte activities against fats and thus facilitate their elimination from the blood.

This specific effect on macrophages is much clearer and more pronounced in the case of a derivative of the β-glucans, β-1,3-D-glucan, which is obtained mainly from beer yeast via β-glucan synthase. β-1,3-D-glucan has proved effective not only in preventing lipid metabolism disorders, but also in stimulating immune defences, in preventing the onset of tumours and in controlling serum glucose.

Macrophage activation, in fact, entails the triggering of a cascade of events which do not merely affect the ability to eliminate pathogenic bacteria, but above all involve the release of cytokines and the stimulation of cell lines such as T cells or spinal cells which are important in the immune response.

It has now surprisingly been found that a composition containing as its characterising components:

(a) isovaleryl L-carnitine or one of its pharmacologically acceptable salts; and
(b) a polysaccharide selected from the group consisting of phosphorylated, glycosylated and aminated glucans and galactans, or mixtures thereof, in which said glucan is selected from the group consisting of β-glucan (oat bran extract), β-1,3-D-glucan (beer yeast extract), β-1,6-D-glucan and mixtures thereof, and said galactan is β-3,6-D-galactan, is extremely effective for the prevention and treatment of disorders related to a reduction of the immune defences and for the prevention and treatment of lipid metabolism disorders, allergic forms and the reduction of organic defences against bacterial or viral infections and tumour processes, as a result of the potent synergistic effect exerted by its components.

The composition may also comprise an additional carnitine selected from the group consisting of L-carnitine, acetyl L-carnitine, propionyl L-carnitine, butyryl L-carnitine and valeryl L-carnitine or their pharmacologically acceptable salts or mixtures thereof.

The weight-to-weight ratio of component (a) to component (b) ranges from 1:0.1 to 1:10, and preferably from 1:0.5 to 1:5.

Reported here below are a number of the most significant tests demonstrating the potent synergistic effect.

Results of Tests Regarding the Immunostimulant and Protective Effect Exerted Against Mitomycin-induced Toxicity by the Combination of Isovaleryl L-carnitine and β-glucan The synergistic action of isovaleryl L-carnitine and β-glucan was proved by tests demonstrating the efficacy of the combination in preventing leukocyte depletion (see Table 1) and in reducing the mortality induced by mitomycin C (see Table 2).

In these tests a first group of mice received peritoneal injections of 50 μg/mouse of mitomycin C for five consecutive days. In addition to mitomycin, a second group of animals were also injected with isovaleryl L-carnitine alone (30 mg/mouse), a third group with β-glucan alone (10 mg/mouse) and a fourth group with a combination of the two compounds for five consecutive days. On the fifth, tenth and twelfth day following the start of treatment, the number of leukocytes present in the blood and the mortality rates of the animals were evaluated in both treated and control animals.

It could thus be noted that on the twelfth day the animals treated with mitomycin C alone presented a 100% mortality rate, while the survival rate of the animals treated with isovaleryl L-carnitine was 15% and that of the mice treated with β-glucan 20%. Practically complete protection was observed with the combination of the two compounds.

Similar results were also observed for the reduction in the number of leukocytes, which was more than 80% in the control animals, but remained practically within normal limits in the animals treated with the combination.

What thus emerges clearly from these tests is the surprising and unexpected synergism of action of the components of the combination according to the present invention.

MACROPHAGE STIMULATION TEST

To demonstrate the action of isovaleryl L-carnitine and β-glucan on macrophage activity, these compounds were placed in contact with human macrophages from bronchoalveolar lavage fluid. After filtration, centrifuging and gradient separation on Ficoll, the viability of the cells was evaluated with the trypan blue test. Phagocytosis and intracellular killing were calculated according to the method described by Lohrer (Lohrer R. I., *J. Bacterial*, 98:996, 1969). The values found indicate that phagocyte activity was increased by approximately 30% by β-glucan and only by 10% by isovaleryl L-carnitine, but that the combination of the two raised this activity by as much as 60%. Equally evident was the increase in intracellular killing the level of which was increased by 15 and 30% with isovaleryl L-carnitine and β-glucan, respectively, whereas the increase was more than 80% when the combination of the two compounds was used. In this case, too, the results demonstrated the potent, unexpected synergistic effect exerted by the components of the composition according to the invention.

TABLE 1

Leukocyte values in animals treated with mitomycin C alone or together with isovaleryl L-carnitine, β-glucan or the two compounds in combination

| Treatment | No. leukocytes after | | |
|---|---|---|---|
| | 5 days | 10 days | 12 days |
| Mitomycin C | 5,400 ± 270 | 3,000 ± 220 | 1,100 ± 190 |
| Isovaleryl L-carnitine | 5,750 ± 310 | 4,900 ± 220 | 3,100 ± 310 |
| β-glucan | 5,950 ± 370 | 5,200 ± 290 | 5,900 ± 410 |
| Isovaleryl L-carnitine + β-glucan | 7,100 ± 430 | 6,600 ± 310 | 6,300 ± 390 |

TABLE 2

Percentage survival values in animals treated with mitomycin C alone or together with isovaleryl L-carnitine, β-glucan or the two compounds in combination

| Treatment | % animals surviving after | | |
|---|---|---|---|
| | 5 days | 10 days | 12 days |
| Mitomycin C | 50 | 20 | 0 |
| Isovaleryl L-carnitine | 50 | 30 | 15 |
| β-glucan | 60 | 35 | 20 |
| Isovaleryl L-carnitine + β-glucan | 100 | 90 | 80 |

Some non-limiting examples of compositions according to the present invention are given hereinbelow:

| 1) | Isovaleryl L-carnitine fumarate | 300 mg |
|---|---|---|
| | β-1,3-D-glucane | 200 mg |
| 2) | Isovaleryl L-carnitine fumarate | 100 mg |
| | Propionyl L-carnitine | 100 mg |
| | Acetyl L-carnitine | 100 mg |
| | Butyryl L-carnitine | 100 mg |
| | β-1,3-D-glucane | 200 mg |
| 3) | Isovaleryl L-carnitine fumarate | 200 mg |
| | β-1,3-D-glucane | 300 mg |
| | β-3,6-D-galactane | 200 mg |
| | β-glucane | 300 mg |
| 4) | Isovaleryl L-carnitine fumarate | 200 mg |
| | β-glucane | 300 mg |
| 5) | Isovaleryl L-carnitine fumarate | 200 mg |
| | L-carnitine fumarate | 100 mg |
| | β-glucane | 300 mg |
| | β-carotene | 2 mg |
| | Pyridoxine | 5 mg |
| | Folic acid | 100 μg |
| | Vit. $B_{12}$ | 100 μg |
| | Vit. E | 5 mg |
| | Vit. C | 50 mg |
| | Coenzyme $Q_{10}$ | 50 mg |

What is meant by a pharmacologically acceptable salt of the various aforesaid carnitines mentioned in the present specification is, in addition to the respective "inner salts", any salt of these with an acid which does not give rise to unwanted toxic or side effects. These acids are well known to pharmacologists and to experts in pharmaceutical technology.

Non-limiting examples of such salts are the following: chloride; bromide; iodide; aspartate, acid aspartate; citrate, acid citrate; tartrate; phosphate, acid phosphate; fumarate, acid fumarate; glycerophosphate; glucose phosphate; lactate; maleate, acid maleate; mucate; orotate; oxalate, acid oxalate; sulphate, acid sulphate; trichloroacetate; trifluoroacetate and methane sulphonate.

Among these salts, isovaleryl L-carnitine acid fumarate (U.S. Pat. No. 5,227,518) is particularly preferred.

A list of FDA-approved pharmacologically acceptable acids is given in *Int. J. Pharm.*, 33, 1986, 201–217, the latter publication being incorporated in the present specification by reference.

The supplement of the invention may further comprise vitamins, coenzymes, mineral substances, aminoacids and antioxidants. The supplement may be manufactured in the form of tablets, lozenges, capsules, pills, granulates, syrups, herb teas, vials or drops.

The invention claimed is:

1. A combination composition consisting of as active ingredients:
   (a) isovaleryl L-carnitine or a pharmacologically acceptable salt thereof; and
   (b) a polysaccharide selected from the group consisting of beta-glucan, beta-1,3 D-glucan, beta-1,6-D-glucan, and mixtures thereof.

2. The composition of claim 1 wherein the weight ratio of (a):(b) is from 1:0.1 to 1:10.

3. The composition of claim 2 wherein the weight ratio of (a):(b) is from 1:0.5 to 1:5.

4. The composition of claim 1 wherein the pharmacologically acceptable salt is selected from the group consisting of chloride; bromide; iodide; aspartate, acid aspartate; citrate, acid citrate; tartrate; phosphate; acid phosphate; fumarate; acid fumarate; glycerophosphate; glucose phosphate; lactate; maleate; acid maleate; mucate; orotate; oxalate; acid oxalate; sulphate; acid sulphate; trichioroacetate; trifluoroacetate and methane sulphonate.

5. The composition of claim 1 which is orally administrable, in the form of a health food or dietary supplement.

6. The composition of claim 5 in the form of a solid, semisolid or liquid preparation.

7. The composition of claim 6 in the dosage form of a tablet, capsule, lozenge, pill, granulate, syrup or drop.

8. The composition of claim 7 in unit dosage form, which consists of:

| Isovaleryl L-carnitine fumarate | 200 mg |
|---|---|
| β-glucan | 300 mg. |

9. The composition of claim 1 which is orally, parenterally, rectally, sublingually or transdermally administrable, in the form of a medicament.

10. A combination composition consisting of as active ingredients:
   (a) isovaleryl L-carnitine or a pharmacologically acceptable salt thereof;
   (b) a polysaccharide selected from the group consisting of beta-glucan, beta-1,3 D-glucan, beta-1,6-D-glucan, and mixtures thereof; and
   (c) beta-3,6-D-galactan.

11. A combination composition consisting of as the active ingredients:
(a) isovaleryl L-carnitine or a pharmacologically acceptable salt thereof;
(b) a polysaccharide selected from the group consisting of beta-glucan, beta-1,3 D-glucan, beta-1,6-D-glucan, and mixtures thereof; and
(c) a carnitine selected from the group consisting of L-carnitine, acetyl L-carnitine, propionyl L-carnitine, butyryl L-carnitine and valery L-carnitine or the pharmacologically acceptable salts or mixtures thereof.

12. The composition of claim 11 in unit dosage form, wherein (a) is 300 mg Isovaleryl L-carnitine fumarate, and (b) is 200 mg beta-1,3-D-glucan.

13. The composition of claim 11 in unit dosage form, which consists of:

| | |
|---|---|
| Isovaleryl L-carnitine fumarate | 100 mg |
| Propionyl L-carnitine | 100 mg |
| Acetyl L-carnitine | 100 mg |
| Butyryl L-carnitine | 100 mg |
| β-1,3-D-glucan | 200 mg. |

14. A composition in unit dosage form, which consists of

| | |
|---|---|
| Isovaleryl L-carnitine fumarate | 200 mg |
| Beta-1,3-D-glucan | 300 mg |
| Beta-3,6-D-galactan | 200 mg |
| Beta-glucan | 300 mg. |

15. A combination composition in unit dosage form, which consists of as the active ingredients:

| | |
|---|---|
| Isovaleryl L-carnitine fumarate | 200 mg |
| L-carnitine fumarate | 100 mg |
| β-glucan | 300 mg |
| β-carotene | 2 mg |
| Pyridoxine | 5 mg |
| Folic acid | 100 μg |
| Vit. $B_{12}$ | 100 μg |
| Vit. E | 5 mg |
| Vit. C | 50 mg |
| Coenzyme $Q_{10}$ | 50 mg. |

16. A method of activating the immune system against bacterial or viral infections which comprises administering to an individual in need thereof a combination composition consisting of the following ingredients:
(a) isovaleryl L-carnitine or a pharmacologically acceptable salt thereof; and
(b) a polysaccharide selected from the group consisting of beta-glucan, beta-1,3 D-glucan, beta-1,6-D-glucan, and mixtures thereof.

17. The method of claim 16 wherein the weight ratio of (a):(b) is from 1:0.1 to 1:10.

18. The method of claim 16 wherein the weight ratio of (a):(b) is from 1:0.5 to 1:5.

19. A method of activating the immune system against bacterial or viral infections which comprises administering to an individual in need thereof a combination composition consisting of the following ingredients:
(a) isovaleryl L-carnitine or a pharmacologically acceptable salt thereof;
(b) a polysaccharide selected from the group consisting of beta-glucan, beta-1,3 D-glucan, beta-1,6-D-glucan, and mixtures thereof; and
(c) a carnitine selected from the group consisting of L-carnitine, acetyl L-carnitine, propionyl L-carnitine, butyryl L-carnitine and valery L-carnitine or the pharmacologically acceptable salts or mixtures thereof.

20. The method of claim 19 wherein the weight ratio of (a):(b) is from 1:0.1 to 1:10.

21. The method of claim 20 wherein the weight ratio of (a):(b) is from 1:0.5 to 1:5.

* * * * *